United States Patent
Hardman et al.

(10) Patent No.: US 9,011,353 B2
(45) Date of Patent: *Apr. 21, 2015

(54) FOOT MANIFOLDS, APPARATUSES, SYSTEMS, AND METHODS FOR APPLYING REDUCED PRESSURE TO A TISSUE SITE ON A FOOT

(71) Applicant: KCI Licensing, Inc., San Antonio, TX (US)

(72) Inventors: Ian James Hardman, Bournemouth Dorset (GB); Colin John Hall, Poole Dorset (GB)

(73) Assignee: KCI Licensing, Inc., San Antonio, TX (US)

( * ) Notice: Subject to any disclaimer, the term of this patent is extended or adjusted under 35 U.S.C. 154(b) by 398 days.

This patent is subject to a terminal disclaimer.

(21) Appl. No.: 13/655,210

(22) Filed: Oct. 18, 2012

(65) Prior Publication Data

US 2013/0041333 A1 Feb. 14, 2013

Related U.S. Application Data

(63) Continuation of application No. 12/404,111, filed on Mar. 13, 2009, now Pat. No. 8,313,449.

(60) Provisional application No. 61/036,433, filed on Mar. 13, 2008.

(51) Int. Cl.
*A61H 7/00* (2006.01)
*A43B 13/20* (2006.01)
(Continued)

(52) U.S. Cl.
CPC .............. *A43B 7/00* (2013.01); *A43B 3/0005* (2013.01); *A61B 5/0002* (2013.01);
(Continued)

(58) Field of Classification Search
CPC .... A43B 7/1465; A43B 7/148; A43B 7/1485; A43B 7/082; A43B 13/20; A43B 13/203; A43B 13/206; A61F 15/008; A61F 13/00068; A61H 9/005; A61H 9/0057

USPC ......... 601/1, 6, 7, 9–11, 84, 88, 96, 104, 105, 601/148, 149, 150–152, 155; 36/43, 44, 28, 36/29, 3 B, 153; 604/304–307, 313, 298, 604/540

See application file for complete search history.

(56) References Cited

U.S. PATENT DOCUMENTS 975,576 A * 11/1910 Sexton .............................. 36/43
1,036,821 A * 8/1912 Flyte ................................ 36/43
(Continued)

FOREIGN PATENT DOCUMENTS

AU 550575 A1 8/1982
AU 745271 4/1999
(Continued)

OTHER PUBLICATIONS

N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986) pp. 94-96 (certified translation).
(Continued)

*Primary Examiner* — Rachel Young
*Assistant Examiner* — LaToya M Louis (57) ABSTRACT

Apparatuses, systems, and methods for applying reduced pressure to a tissue site on a foot are provided. An apparatus may include an insole and a tissue contacting surface covering at least a portion of the insole. At least one portion of the tissue contacting surface is removable to form a void. The apparatus may also include a reduced-pressure interface for receiving reduced pressure from a reduced-pressure source, and at least one flow channel fluidly coupled to the reduced-pressure interface and the void.

11 Claims, 7 Drawing Sheets

(51) Int. Cl.
*A61M 35/00* (2006.01)
*A43B 7/00* (2006.01)
*A43B 3/00* (2006.01)
*A61B 5/00* (2006.01)
*A61B 5/103* (2006.01)

(52) U.S. Cl.
CPC .............. *A61B 5/1036* (2013.01); *A61B 5/447* (2013.01); *A61B 5/6807* (2013.01); *A61B 5/6829* (2013.01); *A61B 2562/0247* (2013.01)

(56) References Cited

U.S. PATENT DOCUMENTS

| | | | |
|---|---|---|---|
| 1,355,846 A | 10/1920 | Rannells | |
| 2,547,758 A | 4/1951 | Keeling | |
| 2,632,443 A | 3/1953 | Lesher | |
| 2,682,873 A | 7/1954 | Evans et al. | |
| 2,909,854 A * | 10/1959 | Edelstein | 36/140 |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,475,836 A * | 11/1969 | Brahm | 36/3 R |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,237,626 A * | 12/1980 | Brown | 36/43 |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,557,060 A * | 12/1985 | Kawashima | 36/44 |
| 4,569,348 A | 2/1986 | Hasslinger | |
| 4,605,399 A | 8/1986 | Weston et al. | |
| 4,608,041 A | 8/1986 | Nielson | |
| 4,640,688 A | 2/1987 | Hauser | |
| 4,654,982 A * | 4/1987 | Lee | 36/3 R |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,841,648 A * | 6/1989 | Shaffer et al. | 36/43 |
| 4,863,449 A | 9/1989 | Therriault et al. | |
| 4,872,450 A | 10/1989 | Austad | |
| 4,878,901 A | 11/1989 | Sachse | |
| 4,888,887 A * | 12/1989 | Solow | 36/3 R |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,068,981 A * | 12/1991 | Jung | 36/3 R |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 5,761,834 A * | 6/1998 | Grim et al. | 36/88 |
| 5,768,803 A * | 6/1998 | Levy | 36/43 |
| 5,806,208 A * | 9/1998 | French | 36/28 |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,360,457 B1 * | 3/2002 | Qui et al. | 36/140 |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,720,470 B2 | 4/2004 | Cavanagh et al. | |
| 6,775,926 B1 * | 8/2004 | Huang | 36/3 B |
| 6,814,079 B2 | 11/2004 | Heaton et al. | |
| 7,681,329 B2 * | 3/2010 | Fu | 36/3 B |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2003/0120194 A1 * | 6/2003 | Stapf | 602/48 |
| 2004/0010939 A1 | 1/2004 | Liu et al. | |
| 2007/0000148 A1 * | 1/2007 | Lin et al. | 36/3 B |
| 2007/0167884 A1 | 7/2007 | Mangrum et al. | |
| 2008/0184600 A1 * | 8/2008 | Yang | 36/3 B |
| 2008/0307679 A1 * | 12/2008 | Chiang et al. | 36/3 B |
| 2009/0282704 A1 * | 11/2009 | Park | 36/3 B |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |

(56) References Cited

FOREIGN PATENT DOCUMENTS

| GB | 2 220 357 A | 1/1990 |
|---|---|---|
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 96/05873 | 2/1996 |
| WO | WO 97/18007 | 5/1997 |
| WO | WO 99/13793 | 3/1999 |
| WO | 2005009488 A2 | 2/2005 |
| WO | 2007092397 A2 | 8/2007 |

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastman, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.

G. Živadinović, V. Ðukić, Ž. Maksimović, Ð. Radak, and P. Peška, "Vacuum Therapy in the Treatment of Peripheral Blood Vessels," *Timok Medical Journal* 11 (1986), pp. 161-164 (certified translation).

F.E. Johnson, "An Improved Technique for Skin Graft Placement Using a Suction Drain," *Surgery, Gynecology, and Obstetrics* 159 (1984), pp. 584-585.

A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," *British Journal of Surgery* 73 (1986), pp. 369-370.

D.E. Tribble, An Improved Sump Drain-Irrigation Device of Simple Construction, *Archives of Surgery* 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).

C.E. Tennants, "The Use of Hypermia in the Postoperative Treatment of Lesions of the Extremities and Thorax," *Journal of the American Medical Association* 64 (1915), pp. 1548-1549.

Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians (Jul. 2007).

\* cited by examiner

FOOT MANIFOLDS, APPARATUSES, SYSTEMS, AND METHODS FOR APPLYING REDUCED PRESSURE TO A TISSUE SITE ON A FOOT

CROSS-REFERENCE TO RELATED APPLICATIONS

This application is a continuation of U.S. patent application Ser. No. 12/404,111, entitled "FOOT MANIFOLDS, APPARATUSES, SYSTEMS, AND METHODS FOR APPLYING REDUCED PRESSURE TO A TISSUE SITE ON A FOOT," filed Mar. 13, 2009, which application claims the benefit of U.S. Provisional Application No 61/036,433 filed Mar. 13, 2008, which is hereby incorporated by reference.

BACKGROUND

The illustrative embodiments relate generally to medical treatment systems and, more particularly, to foot manifolds, apparatuses, systems, and methods for applying reduced pressure to a tissue site on a foot.

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue.

SUMMARY

According to an illustrative embodiment, an apparatus for applying reduced pressure to a tissue site on a foot includes an insole and a tissue contacting surface covering at least a portion of the insole. At least one portion of the tissue contacting surface is removable to form a void. The apparatus may also include a reduced-pressure interface for receiving reduced pressure from a reduced-pressure source, and at least one flow channel fluidly coupled to the reduced-pressure interface and the void.

In one illustrative embodiment, a system may include, in addition to the apparatus described above, a reduced-pressure source operable to supply reduced pressure. The system may also include a delivery conduit operable to deliver reduced pressure from the reduced-pressure source to the reduced-pressure interface of the apparatus.

In one illustrative embodiment, a method for applying reduced pressure to a tissue site on a foot includes providing a foot manifold and removing a portion of a tissue contacting surface that covers an insole of the foot manifold to form a void. The method also includes aligning the void with the tissue site on the foot and creating a substantially pneumatic seal between the void and the tissue site. The method also includes applying reduced pressure from a reduced-pressure source to the void via a flow channel such that reduced pressure is applied to the tissue site.

In one illustrative embodiment, a method of manufacturing an apparatus for applying reduced pressure to a tissue site on a foot includes providing an insole and providing a tissue contacting surface. The method also includes covering at least a portion of the insole with the tissue contacting surface to form at least one flow channel operable to transfer reduced pressure.

Other objects, features, and advantages of the illustrative embodiments will become apparent with reference to the drawings and detailed description that follow.

DETAILED DESCRIPTION

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1:
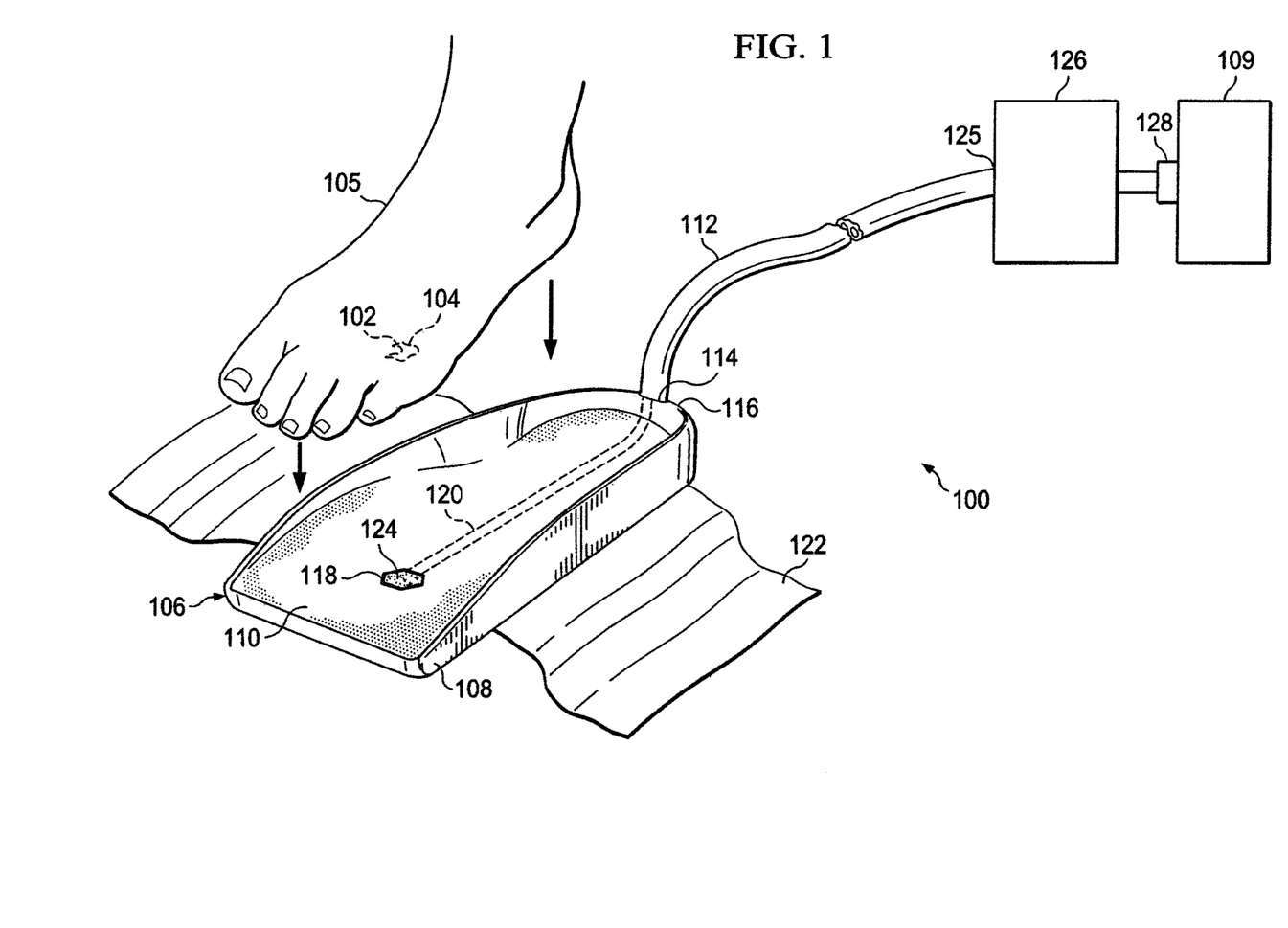
FIG. 1 illustrates a perspective view of a system for applying reduced pressure to a tissue site on a foot according to an illustrative embodiment.

Referring to FIG. 1, an illustrative embodiment of a reduced-pressure treatment system 100 for providing reduced-pressure treatment to a tissue site 102, such as a wound 104, on a foot 105 of a patient is presented. The reduced-pressure treatment system 100 includes a foot manifold 106 that receives reduced pressure from a reduced-pressure source 109, and which supplies reduced pressure to a tissue site on the foot 105. The foot manifold 106 includes an insole 108, and a tissue contacting surface 110 that covers the tissue facing surface of the insole 108. As used herein, "covers" includes fully or partially covering. The reduced pressure may be delivered to the foot manifold 106 through a delivery conduit 112, which may be inserted, or otherwise removably coupled, to a reduced-pressure interface 114 located at the rear 116 of the insole 108. A portion of the tissue contacting surface 110 is removable to form a void 118, which may be aligned with the wound 104 when the foot manifold 106 and foot 105 are adjacent. One or more flow channels 120 in the insole 108 transfers reduced pressure from the reduced-pressure interface 114 to the void 118 such that reduced-pressure treatment is delivered to the wound 104.

As used herein, "reduced pressure" generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site. In one embodiment, the reduced pressure may initially generate fluid flow in the delivery conduit 112 and proximate the wound 104. As the hydrostatic pressure around the wound 104 approaches the desired reduced pressure, the flow may subside, and the reduced pressure may be maintained. Unless otherwise indicated, values of pressure stated herein are gauge pressures. The reduced pressure delivered may be static or dynamic (patterned or random) and may be delivered continuously or intermittently. Although the terms "vacuum" and "negative pressure" may be used to describe the pressure applied to the tissue site, the actual pressure applied to the tissue site may be more than the pressure normally associated with a complete vacuum. Consistent with the use herein, an increase in reduced pressure or vacuum pressure typically refers to a relative reduction in absolute pressure. Unless otherwise indicated, as used herein, "or" does not require mutual exclusivity.

The wound 104 may be any type of wound, or damaged area of tissue, and may include wounds from trauma, surgery, or other causes, such as a diabetic ulcer. The tissue site 102, which includes the wound 104, may be the bodily tissue of any human, animal, or other organism, including bone tissue, adipose tissue, muscle tissue, dermal tissue, vascular tissue, connective tissue, cartilage, tendons, ligaments, or any other tissue. Treatment of the tissue site 102 may include removal of fluids, e.g., exudate, or delivery of reduced pressure.

In the example in which the wound 104 is a foot ulcer, the insole 108 may also serve to off-load pressure from the wound 104, such as when the patient is walking or standing. The tissue contacting surface 110 may maintain contact with the tissue around the wound 104, thereby relieving pressure from the wound 104. The pressure exerted upon the wound 104 is reduced due to the presence of the void 118 adjacent the wound 104. In particular, because the portion of the tissue contacting surface 110 that is adjacent the wound 104 is removed, the pressure exerted upon the wound 104 is reduced.

The foot manifold 106 may be used in conjunction with or in lieu of therapeutic casting systems, such as total contact casting and removable cast walkers. For example, the foot manifold 106 may be placed into a therapeutic casting, system that is worn by the patient. In another example, the foot manifold 106 may be inserted into any article of footwear, such as a shoe, boot, sandal, or sock.

The foot manifold 106 may also be secured to the foot 105 in other ways. For example, a securing member 122 may be at least partially wrapped around the insole 108 and the foot 105. Adhesive may be used to prevent the securing member 122 from unwrapping. If desired, the foot 105 and the foot manifold 106 that have been wrapped by the securing member 122 may be placed in footwear, including a therapeutic casting system. The foot manifold 106 may also be secured to the foot 105 using one or more elastic bands that press the foot manifold 106 and foot 105 against one another.

In another example, the foot manifold 106 may adhere to the foot 105 without the need for the securing member 122 or footwear. In this example, the tissue contacting surface 110 of the foot manifold 106 may be made from or coated with an adhesive material that secures the foot 105 to the foot manifold 106.

A foam manifold 124 may be inserted into the void 118. The foam manifold 124 assists in applying reduced pressure to, delivering fluids to, or removing fluids from the wound 104. The foam manifold 124 typically includes a plurality of flow channels or pathways that are interconnected to improve distribution of fluids provided to and removed from the wound 104 adjacent the foam manifold 124. The foam manifold 124 may be a biocompatible material that is capable of being placed in contact with the wound 104 and distributing reduced pressure to the wound 104. Examples of foam manifolds 124 may include, for example, without limitation, devices that have structural elements arranged to form flow channels, such as, for example, cellular foam, open-cell foam, porous tissue collections, liquids, gels, and foams that include, or cure to include, flow channels. The foam manifold 124 may be porous and may be made from foam, gauze, felted mat, or any other material suited to a particular biological application. In one embodiment, the foam manifold 124 is a porous foam and includes a plurality of interconnected cells or pores that act as flow channels. The porous foam may be a polyurethane, open-cell, reticulated foam, such as a GranuFoam® material manufactured by Kinetic Concepts, Incorporated of San Antonio, Tex. In some situations, the foam manifold 124 may also be used to distribute fluids, such as medications, antibacterials, growth factors, and various solutions to the wound 104. Other layers may be included in or on the foam manifold 124, such as absorptive materials, wicking materials, hydrophobic materials, and hydrophilic materials.

Reduced pressure is delivered to the void 118 through the flow channel 120. Although the foot manifold 106 is shown to have only a single flow channel 120, the foot manifold 106 may have any number of flow channels, such as flow channel 120, that are able to fluidly connect any portion of the insole 108 or tissue contacting surface 110 with the reduced-pressure interface 114. As described in the figures below, these flow channels may be interconnected, form any pattern, or defined by one or more grooves on the insole 108 or the tissue contacting surface 110. The flow channel 120 may also be a tube or conduit that fluidly couples the reduced-pressure interface 114 to the void 118.

Reduced pressure is delivered to the flow channel 120 via the reduced-pressure interface 114. The reduced-pressure interface 114 may be any socket, port, hole, or other attachment capable of facilitate coupling, including the fluid coupling, between the delivery conduit 112 and the foot manifold 106. As used herein, the term "coupled" includes coupling via a separate object and includes direct coupling. The term "coupled" also encompasses two or more components that are continuous with one another by virtue of each of the components being formed from the same piece of material. Also, the term "coupled" may include chemical, such as via a chemical bond, mechanical, thermal, or electrical coupling. Fluid coupling means that fluid is in communication between the designated parts or locations.

In one non-limiting example, the reduced-pressure interface 114 may include a hole into which the delivery conduit 112 may be inserted, thereby forming an interference fit.

Upon insertion of the delivery conduit 112 into the reduced-pressure interface 114, reduced pressure may be delivered to the flow channel 120 and the void 118 from the reduced-pressure source 109. A mechanism may also be used to secure the delivery conduit 112 to the reduced-pressure interface 114 to prevent the delivery conduit 112 from being pulled out of the reduced-pressure interface 114. In one embodiment, the delivery conduit 112 is integrally formed with the reduced-pressure interface 114 such that the delivery conduit 112 is fixedly coupled to the reduced-pressure interface 114. The reduced-pressure interface 114 may also include a swivel, hinge, or other movable attachment mechanism to permit the delivery conduit 112 to move or swivel relative to the insole 108.

The delivery conduit 112 may include one or more lumens through which a fluid may flow. In one embodiment, the delivery conduit 112 includes two or more lumens, any of which may be used to transfer reduced pressure to the foot manifold 106, transfer liquid, such as exudate, away from the foot manifold 106, or transfer therapeutic fluids to the foot manifold 106.

The reduced-pressure source 109 provides reduced pressure to the foot manifold 106. The reduced-pressure source 109 may be any means of supplying a reduced pressure, such a vacuum pump. While the amount and nature of reduced pressure applied to a site will typically vary according to the application, the reduced pressure will typically be between −5 mm Hg and −500 mm Hg.

A medial portion 125 of the delivery conduit 112 may have one or more devices, such as device 126. For example, the device 126 might be another fluid reservoir, or collection member to hold exudates and other fluids removed. Other examples of the device 126 that might be included on the medial portion 125 of the delivery conduit 112 or otherwise fluidly coupled to the delivery conduit 112 include the following non-limiting examples: a pressure-feedback device, a volume detection system, a blood detection system, an infection detection system, a flow monitoring system, a temperature monitoring system, etc. Some of these devices may be formed integral to the reduce-pressure source 109. For example, a reduced-pressure port 128 on the reduced-pressure source 109 may include a filter member that includes one or more filters, e.g., an odor filter.

In use, a patient or caretaker may remove a portion of the tissue contacting surface 110 to form the void 118. The portion of the tissue contacting surface 110 that is removed is detachably mated to the insole 108, and may be chosen such that the void 118 aligns, or is otherwise adjacent, the wound 104 when the foot manifold 106 and the foot 105 are adjacent one another. Grid lines or markers may be included on the tissue contacting surface 110 to assist in choosing the appropriate portion of the tissue contacting surface 110 for removal. The foam manifold 124 may be inserted into the void 118. When in use, the foot 105 and the foot manifold 106 are disposed adjacent one another to create a substantially pneumatic seal between the void 118 and the wound 104. As described below, the substantially pneumatic seal may be facilitated in variety of ways, including through the use of a sealing member (not shown) or the tissue contacting layer 110 itself. Reduced pressure may then be applied to the foot manifold 106 from the reduced-pressure source 109. The reduced pressure may be transferred through the delivery conduit 112 and into the void 118 via the reduced-pressure interface 114 and the flow channel 120, thereby providing reduced-pressure treatment to the wound 104. The substantially pneumatic seal formed at the wound 104 helps to maintain the reduced pressure at therapeutic levels.

Referring to FIGS. 2, 3A-B, and 4A-B, an illustrative embodiment of the foot manifold 206 includes the insole 208. The foot manifold 206 also includes support members 232, which are functionally analogous to the tissue contacting surface 110 in FIG. 1.

Figure 2:
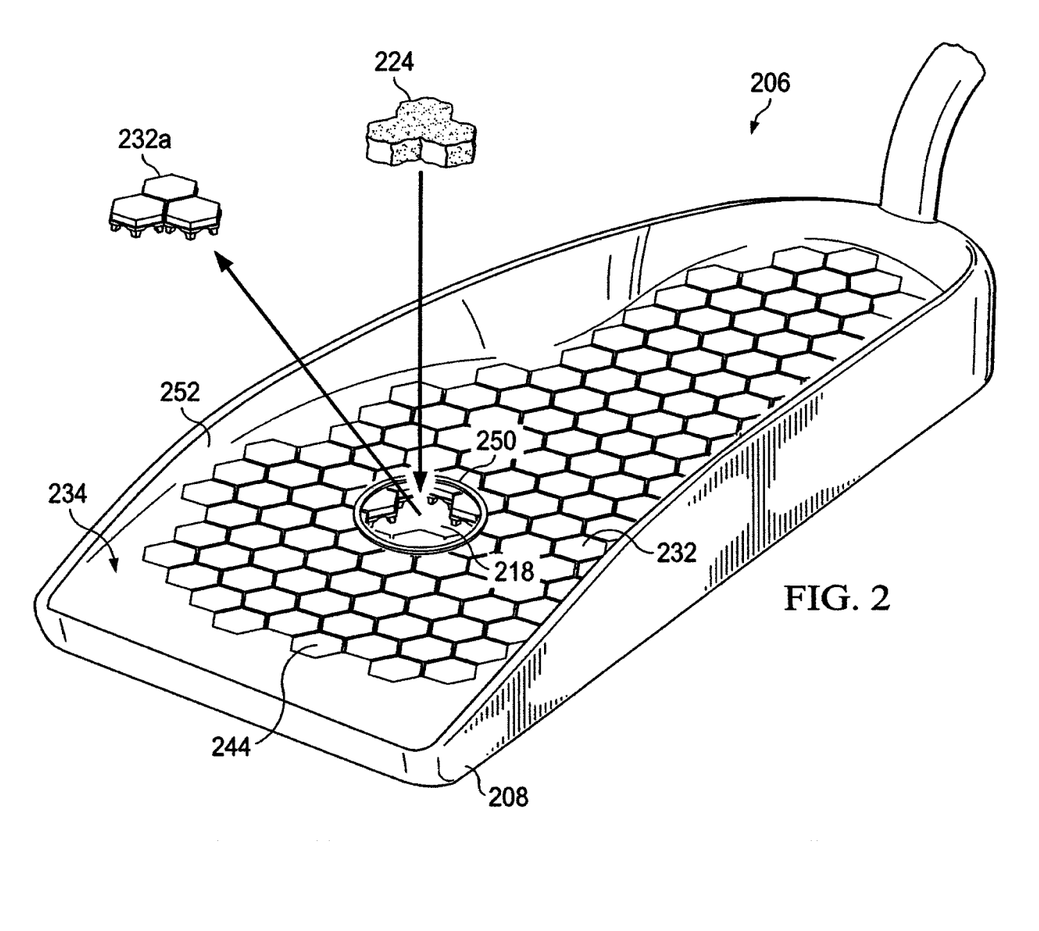
FIG. 2 illustrates a perspective view of an apparatus for applying reduced pressure to a tissue site on a foot according to an illustrative embodiment.

In one embodiment, the insole 208 is shaped and sized to approximate the plantar region 230 of the foot 205, but may also cover only a portion of the plantar region 230, such as the heel region. The insole 208 may also cover all or a portion of the dorsal region, toes, sides, or rear of the foot 205. The insole 208 includes a ridge 252, which may help to secure the foot 205 to the foot manifold 206 and prevent movement of the insole 208 relative to the foot 205 or the wound 204. In another example, the insole 208 does not have the ridge 252.

The insole 208 may be formed from any material. For example, the insole 208 may be composed of a flexible or elastic material, such as silicon, polyurethane, or a thermoplastic elastomer. The flexible or elastic composition of the insole 208 may also facilitate the insertion of the insole 208 into an article of footwear.

The support members 232 form a layer that covers a tissue facing surface 234 of the insole 208. The support members 232 contact the plantar region 230 of the foot 205, and may provide an off-loading function that can reduce the pressure exerted on the wound 204. Although shown as hexagonal, the support members 232 may have any shape, including, without limitation, a square, rectangle, triangle, octagon, polygon, circle, oval, or irregular shape.

The flow channels 220 are disposed between the support members 232 and the insole 208, and are formed by a tissue facing surface 254 of the insole 208 and the grooves 236 on the insole-facing side 237 of the support members 232. The grooves 236 may be formed along three axes 238, 239, 240. Each side 242 of the support member 232 may include a groove 236. However, some support members 232, such as those support members on the periphery 244 of the layer formed by the support members 232, may have sides 242 that do not include a groove 236. When the support members 232 cover the insole 208, the grooves 236 form an interconnected network of flow channels 220 that distributes reduced pressure along the interface 245 between the support members 232 and the insole 208. The support members 232 comes into contact with the insole 208, or may be coupled to the insole 208 using any, known technique, including without limitation welding (e.g., ultrasonic or RF welding), bonding, adhesives, cements, etc. In one embodiment, the support members 232 are coupled to the insole 208 to seal the flow channels 220 and keep reduced pressure from leaking out of the flow channels 220 leading to the void 218.

Figure 4A:
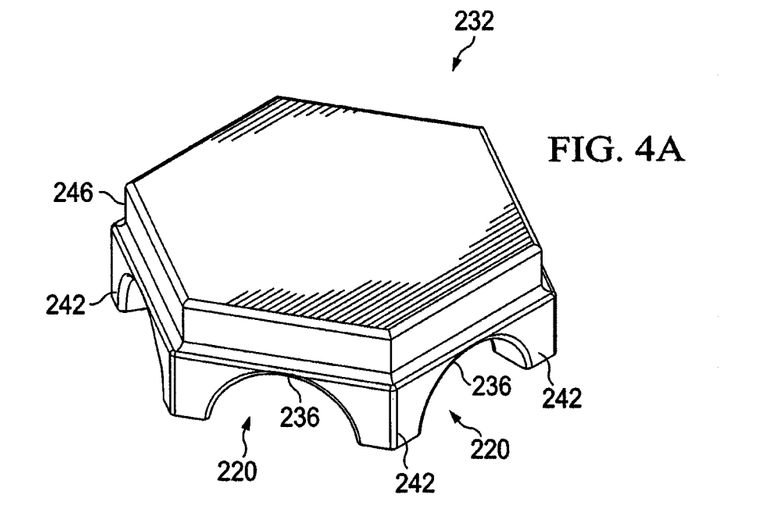
FIG. 4A illustrates a top perspective view of a support member of the apparatus of FIG. 2.
Figure 4B:
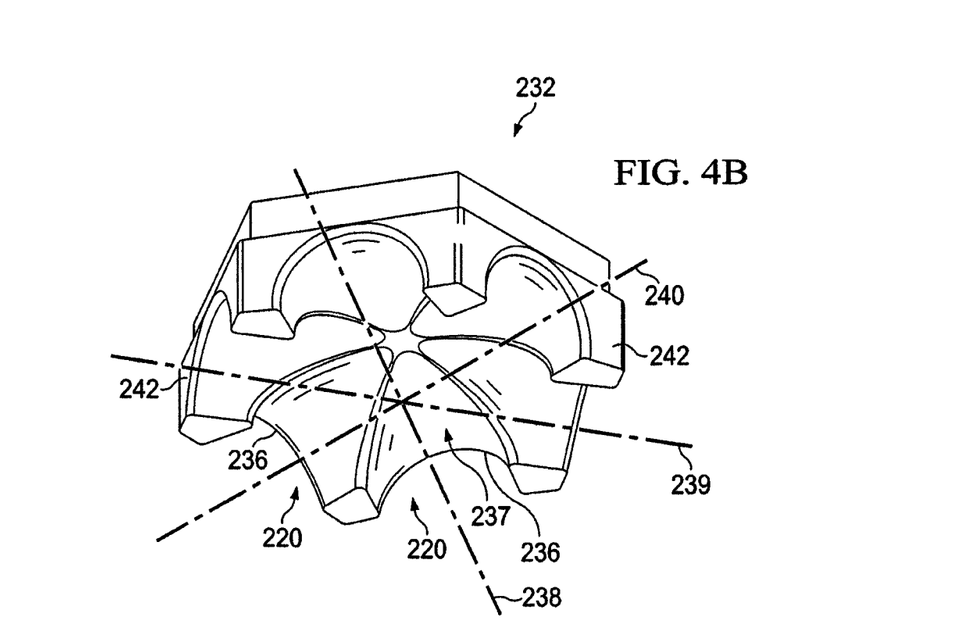
FIG. 4B illustrates a bottom perspective view of the support member of FIG. 4A.

In one embodiment, the grooves 236 are arch-shaped grooves. However, the grooves 236 may have any shape. For example, the grooves 236 may have one or more straight side walls such that, when the support member 232 is coupled to the insole 208, an at least partially polygonal flow channel is formed.

The support members 232 may include one or more insertion slots 246. The insertion slots 246 may be adapted to receive a device that facilitates the removal of each of the support members 232, such as a scalpel. The insertion slots 246 may have any shape, and the shape may depend upon the type of device to be used in the removal of the support members 232.

The support members 232 at the periphery 244 include lap joints 248. In one example, the lap joints 248 are included only on those support members 232 on the periphery 244 of the layer formed by the support members 232. The lap joints 248 facilitate a sealed connection between the support members 232 and the insole 208. Although the lap joints 248 are shown to be polygonal protrusions, the lap joints 248 may also be rounded protrusions or any other protrusion that can facilitate a sealed connection between the support members 232 and the insole 208.

The support members 232 may also be made of any material capable of supporting the foot 205. For example, each of the support members 232 may be made of elastic, flexible, or soft materials. The elastic qualities of the support members 232 may lessen the pressure exerted upon the tissue site. Non-limiting examples of the material from which the support members 232 may be composed include silicon (including soft, conformable silicon), polyurethane, and a thermoplastic elastomer (TPE).

Any one or more of the support members 232 may be removed to form the void 218. In FIG. 2, support members 232a are removed to form the void 218. The support members 232a may be chosen based on their location on the insole 208 such that the wound 204 is adjacent the void 218 when the foot 205 is placed adjacent the foot manifold 206. Markers, such as characters, may be included on the support members 232 to help locate the support members 232a that align with the wound 204. A sealing member 250 may be disposed around the void 218 and between the foot 205 and the support members 232 when the foot 205 is applied to the foot manifold 206. The foot 205 may be positioned on the sealing ring 250 and the support members 232 such that a seal is formed at the void 218. The seal that is formed by the sealing member 250 helps to prevent the escape of reduced pressure from the void 218 such that a therapeutic reduced pressure may be maintained at the void 218 and applied to the wound 204.

The sealing member 250 may have any shape and may be made of any material that helps to form a seal at the void 218. For example, the sealing member 250 may be a hydrogel ring. The sealing member 250 may also be formed from putty, silicon, closed cell polymer foam, TPE, or a soft, flexible, elastic, or adhesive material.

Upon removing the support members 232a, the void 218 may be fully or partially filled with the foam manifold 224. Before placement into the void 218, the foam manifold 224 may be smaller, larger, or approximately equal in volume to the void 218. The shape of the foam manifold 224 may also be any predetermined shape, or customized to fit the void 218. Also, the foam manifold 224, once inserted into the void 218, may expand to fill the void 218, and may press against the insole 208 or the support members 232 adjacent the void 218.

In one embodiment, the foam manifold 224 may be torn or cut from a foam sheet. The foam sheet may also be pre-cut to include foam manifold 224 that approximate the size of the void 218, or the size of the support member 232. In an alternate embodiment, the foam manifold 224 may be placed into or on the wound 204 prior to applying the foot 205 to the foot manifold 206. In another embodiment, no foam manifold 224 need be used when treating the wound 204 with reduced pressure.

Figure 3A:
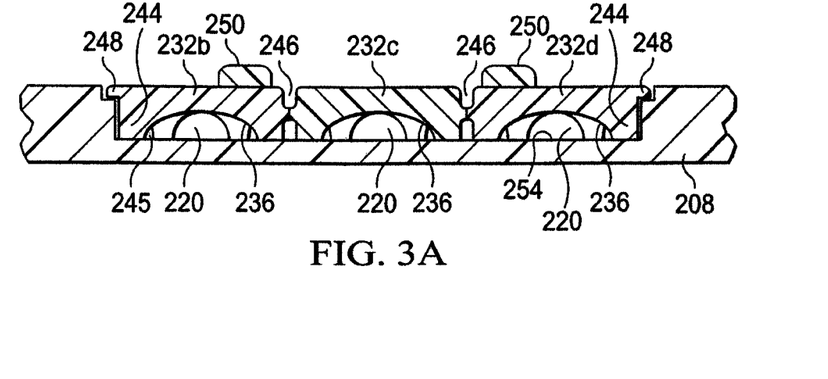
FIG. 3A illustrates a cross-sectional view of the apparatus of FIG. 2.
Figure 3B:
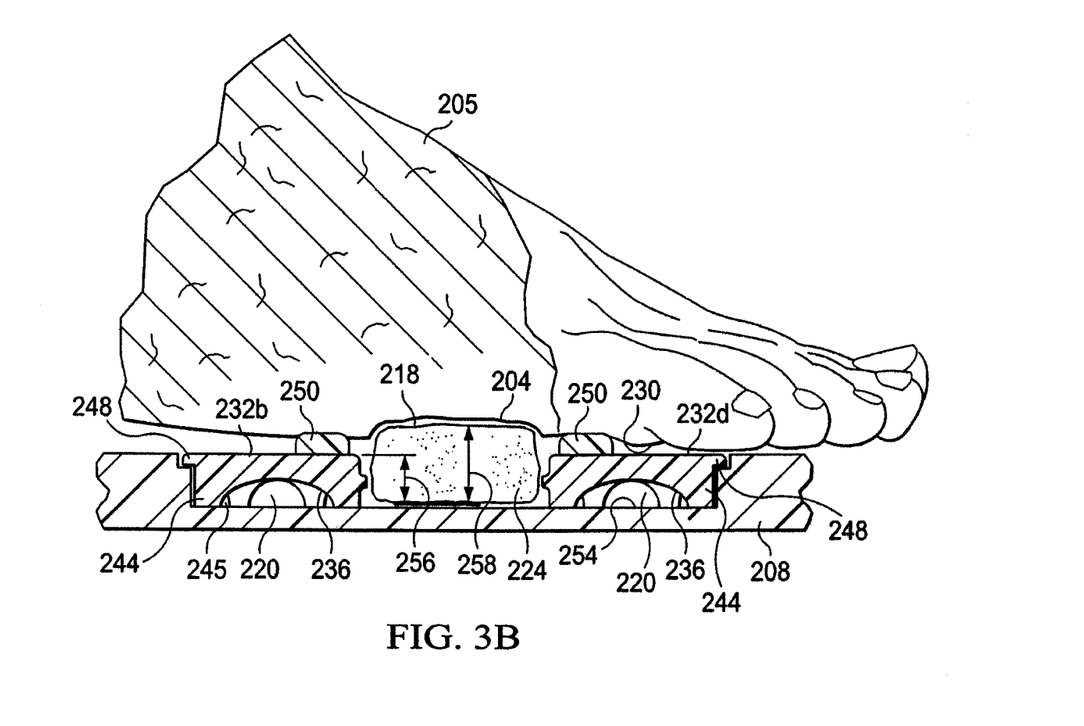
FIG. 3B illustrates a cross-sectional view of the apparatus of FIG. 2, the apparatus having a support member removed to form a void.

The foam manifold 224 in the void 218 may have a height 256 that approximates the height of the support members 232. The foam manifold 224 may also have a height 258 that is greater than the height of the support members 232, and which may touch the wound 204. In another embodiment, the foam manifold 224 is shorter than the height 256 of the support member 232.

In FIG. 3B, support member 232c, which is disposed between support members 232b and 232d in FIG. 3A, has been removed to form the void 218. Reduced pressure that is applied to the foot manifold 206 passes through the interconnected flow channels 220 formed by the grooves 236 and the tissue facing surface 254 of the insole 208 to reach the void 218. As explained above, the sealing member 250 may be used to create a seal at the void 218 such that a therapeutic reduced pressure is maintained at the void 218 and applied to the wound 204. In the illustrative embodiments, reduced pressure may be applied only to those portions of the foot 205 at which reduced-pressure treatment is desired, while supporting the remainder of the foot 205 using the support members 232.

Figure 5:
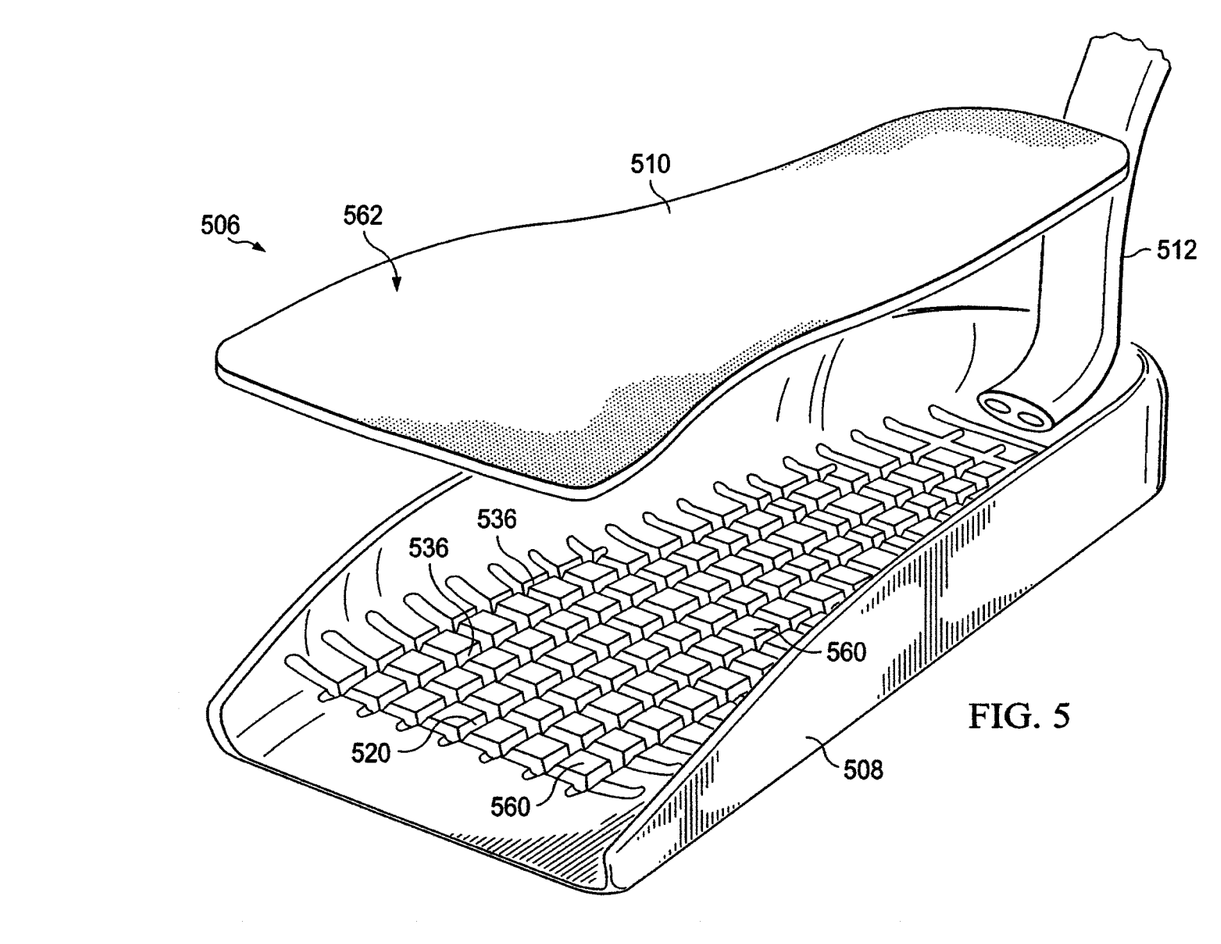
FIG. 5 illustrates an exploded perspective view of an apparatus for applying reduced pressure to a tissue site on a foot according to an illustrative embodiment.
Figure 6:
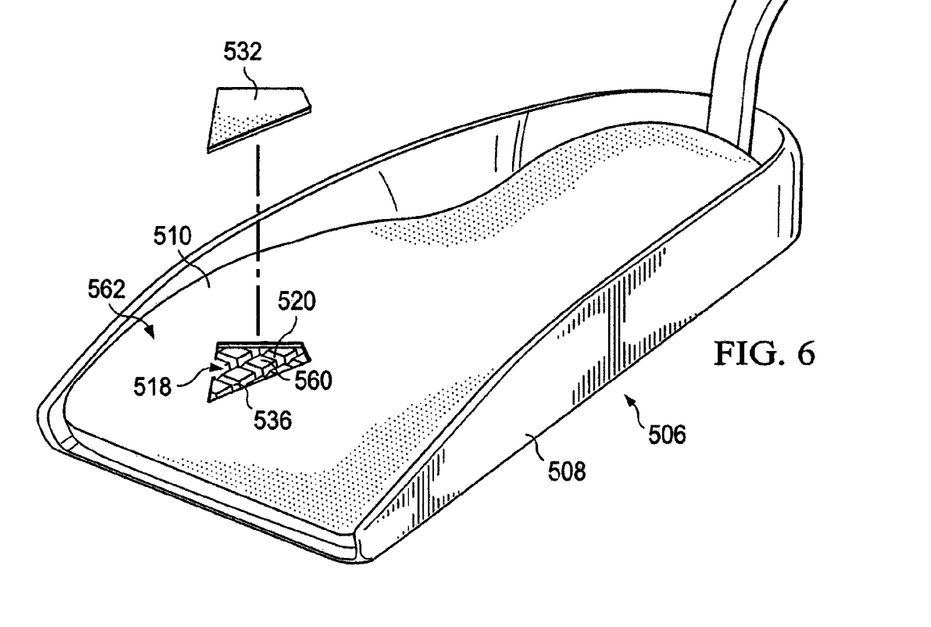
FIG. 6 illustrates a perspective view of the apparatus of FIG. 5 with a portion of a sealing layer removed to form a void.

Referring to FIGS. 5 and 6, a foot manifold 506 that includes a sealing layer 510 is shown according to an illustrative embodiment. The sealing layer 510 is functionally analogous to the tissue contacting layer 110 in FIG. 1. The sealing layer 510 is bonded, or otherwise coupled, to the insole 508, and covers all or a portion of the insole 508.

The insole 508 includes a flow channels 520, which are interconnected and formed by grooves 536 and protrusions 560 in the insole 508. The flow channels 520 form a grid. However, the flow channels 520 may form any pattern, including irregular patterns or no pattern at all. The flow channels 520 are further defined by an insole-contacting side of the sealing layer 510 when the sealing layer 510 abuts the insole 508. Reduced pressure may be provided to the flow channels 520 via the delivery conduit 512.

The sealing layer 510 may be composed of any material. For example, the sealing layer 510 may be composed of a flexible material that is capable of providing a sealed connection between the sealing layer 510 and the insole 508. In one non-limiting example, the sealing layer 510 may be a hydrogel layer. The tissue-facing side 562 or the insole-facing side of the sealing layer 510 may be adhesive. Adherence between the tissue-facing side 562 of the sealing layer 510 and the foot 105 may help to secure the foot 105 to the foot manifold 506.

A portion 532 may be identified, cut, and removed from the sealing layer 510 to form the void 518. The portion 532 may be removed using any device capable of cutting the sealing layer 510, such as a scalpel. A foam manifold may be inserted into the void 518. A foot may be disposed on top of the sealing layer 510 such that a tissue site, such as a wound, on the foot abuts the void 518. Reduced pressure may be transferred to the flow channels 520 via the delivery conduit 512, and the reduced pressure may be transferred through the flow channels 520 to the void 518.

The sealing characteristics of the sealing layer 510 help to prevent reduced pressure that is transferred to the void 518 from escaping, thereby maintaining a therapeutic reduced pressure for the tissue site abutting the void 518. The sealing layer 510 may thus eliminate the need for a sealing member. Using the sealing layer 510, the void 518 may be located anywhere on the sealing layer 510, and the portion 532 of the sealing layer 510 that is removed to form the void 518 may have any shape. The location and shape of the removed portion 532 may be determined based on a location and shape of a wound on a foot, such as a foot ulcer. Grid markers, such as grid lines, may be printed, or otherwise included, on the sealing layer 510 to help identify the portion of the sealing layer 510 that should be removed to align the void 518 with a wound on a foot. The grid markers may also help to determine the healing progress of the wound as the sealing layer 510 is replaced during overall treatment of the wound.

Figure 7:
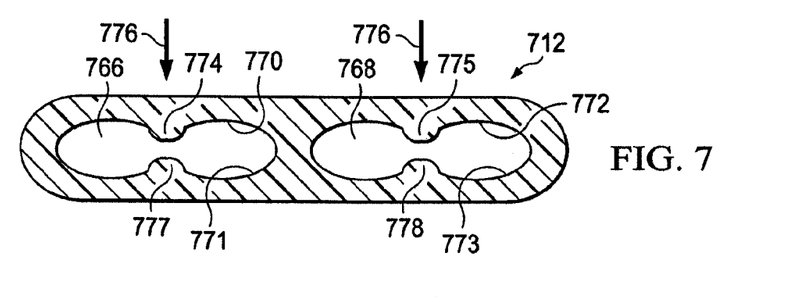
FIG. 7 illustrates a cross-sectional view of a delivery conduit according to an illustrative embodiment.

Referring to FIG. 7, a delivery conduit 712 that is functionally analogous to the delivery conduit 112 in FIG. 1 is shown according to an illustrative embodiment. The delivery conduit 712 has an elongated shape having a low profile. The elongated shape of the delivery conduit 712 alleviates the pressure points applied to the portions of the foot, ankle, or leg that are adjacent the delivery conduit 712. The delivery conduit 712 may also have other shapes, such as a circular, elliptical, polygonal, or curved "U" shape.

The delivery conduit 712 may also be made of any material, such as a flexible, elastic, or compressible material. The flexible, elastic, or compressible material may alleviate the pressure points applied to adjacent portions of the foot, ankle, or leg. Non-limiting examples of material from which the delivery conduit 712 may be formed include plastic, nylon, silicon, polyurethane, TPE, or PVC.

The delivery conduit 712 includes two lumens 766, 768. In one example, the lumens 766, 768 transfer reduced pressure to one or more flow channels in a foot manifold. The delivery conduit 712 may have any number of lumens, including three or more lumens. In addition, one or more of the lumens in the delivery conduit 712 may be used to transport fluid, such as liquid or exudate, from a wound to a fluid collection apparatus. In other embodiments, the lumens 766, 768 may have any shape, such as a circular, elliptical, or polygonal shape.

The lumen 766 is bound by a first wall 770 and a second wall 771. Similarly, the lumen 768 is bound by a first wall 772 and a second wall 773. The first walls 770, 772 include protrusions 774, 775, respectively. The protrusion 774 prevents the first wall 770 from touching the second wall 771 when a force is applied to the delivery conduit 712 in a direction indicated by arrows 776. The protrusion 775 prevents the first wall 772 from touching the second wall 773 when a force is applied to the delivery conduit 712 in a direction indicated by arrows 776. In this manner, the protrusions 774, 775 help prevent the lumens 766, 768 from collapsing.

The second walls 771, 773 include protrusions 777, 778, respectively. The protrusion 774 touches protrusion 777 when a force is applied to the delivery conduit 712 in a direction indicated by arrows 776 such that the portion of the first wall 770 and the second wall 771 that do not have protrusions 774 and 777 do not touch one another. Similarly, the protrusion 775 touches protrusion 778 when a force is applied to the delivery conduit 712 in a direction indicated by arrows 776 such that the portion of the first wall 772 and the second wall 773 that do not have protrusions 775 and 778 do not touch one another. The lumens 766, 768 may be prevented from collapsing in this manner.

Figure 8:
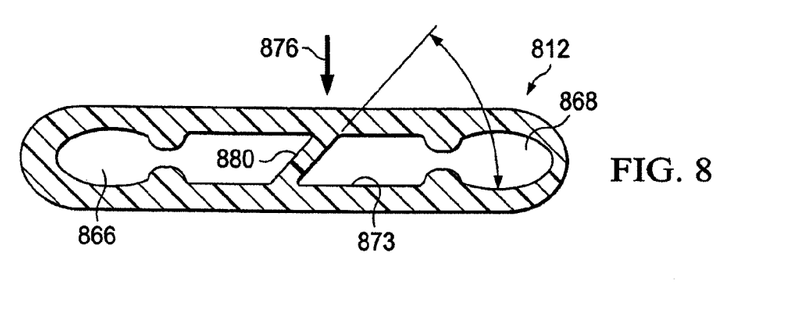
FIG. 8 illustrates a cross-sectional view of a delivery conduit according to an illustrative embodiment.

Referring to FIG. 8, the delivery conduit 812 includes an angled divider 880, which separates lumens 866, 868 from one another. The angled divider 880 may alleviate pressure points on a foot, ankle, or leg when the foot, ankle, or leg presses against the delivery conduit 812 in a direction indicated by arrow 876. In this example, the angled divider 880 may flatten when the foot, ankle, or leg presses against the delivery conduit 812 in a direction indicated by arrow 876. The angled divider 880 may form an approximately 45 degree angle with the wall 873 of the lumen 868, or any other lumen wall in the delivery conduit 812.

Figure 9:
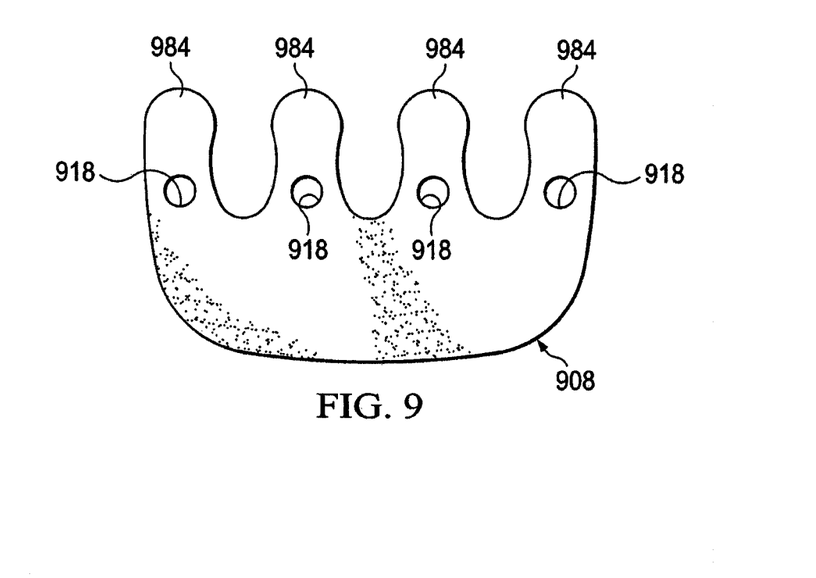
FIG. 9 illustrates a top view of an apparatus for applying reduced pressure to a tissue site on a foot according to an illustrative embodiment.
Figure 10:
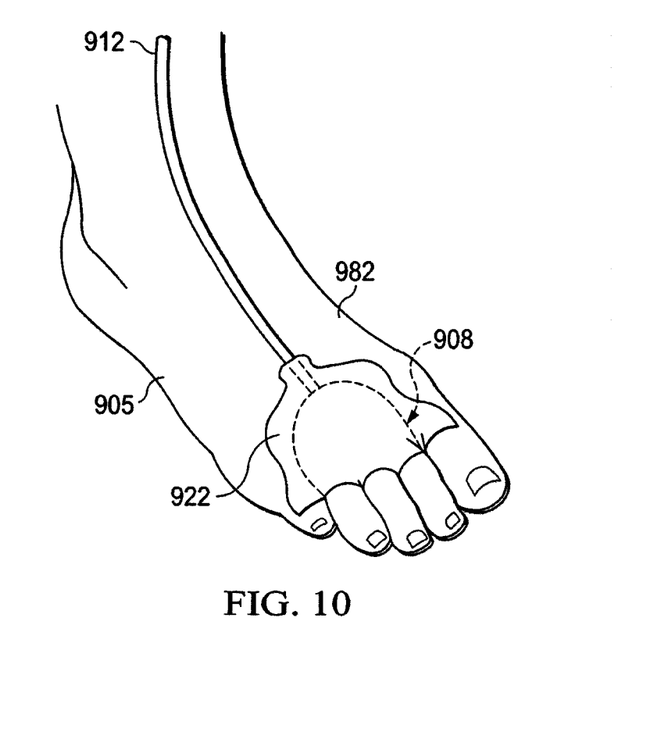
FIG. 10 illustrates a perspective view of the apparatus of FIG. 9 applied to a tissue site on a foot according to an illustrative embodiment.

Referring to FIGS. 9 and 10, an insole 908 is shown according to an illustrative embodiment. The insole 908 may be placed on a dorsal region 982 of the foot 905, and, in particular, at the toe region of the foot 905. In one example, the insole 908 may be composed of a foam, such as reticulated foam or a GranuFoam® material. The insole 908 may be coupled to the toe region of the foot 905 via the securing member 922. Reduced pressure may be applied to the toe region by the insole 908 using reduced pressure that is delivered from a reduced-pressure source and delivered via the delivery conduit 912.

The insole 908 includes protrusions 984, which may be inserted between the toes of the foot 905. The insole 908 may also include voids 918 through which reduced pressure may be applied to a region between the toes of the foot 905. In another non-limiting example, each of the protrusions 984 may be placed on an individual toe of the foot 905. The protrusions 984 may have any shape that facilitates the application of reduced pressure to the desired portion of the toe region of the foot 905.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in a connection to any one embodiment may also be applicable to any other embodiment.

What is claimed is:

1. An apparatus for applying reduced pressure to a tissue site on a foot, the apparatus comprising:
    an insole having a surface;
    a plurality of support members having a first surface facing and covering at least a portion of the surface of the insole and a second surface for contacting the tissue site, a portion of the plurality of support members each having a groove located in the first surface but not in the second surface and at least one of the plurality of support members being removable to form a void;
    a reduced-pressure interface for receiving reduced pressure form a reduced-pressure source;
    a flow channel formed from a plurality of interconnected flow channels each formed by one of the grooves and the surface of the insole, the flow channel being fluidly coupled between the void and the reduced-pressure interface for providing a reduced pressure to the void.

2. The system of claim 1, wherein at least one edge of each of the plurality of removable support members defines at least a portion of an insertion slot, the insertion slot adapted to receive a device that facilitates removing each of the plurality of removable support members.

3. The system of claim 1, wherein the at least one flow channel contains a tube transferring reduced pressure from the reduced pressure interface to the void.

4. The system of claim 1, further comprising:
    a sealing member operable to substantially seal the void, the sealing member adapted to be disposed between the plurality of removable support members and the tissue site.

5. The system of claim 1, wherein the at least one flow channel is at least partially formed by a groove on the insole.

6. The system of claim 5, wherein the groove on the insole forms a grid pattern.

7. The system of claim 1, further comprising:
    a foam manifold adapted to be inserted into the void, and further adapted to distribute reduced pressure to the tissue site.

8. The system of claim 1, further comprising:
    a delivery tube coupled to the reduced-pressure interface and operable to transfer reduced pressure from the reduced pressure source to the reduced-pressure interface.

9. The system of claim 8, wherein the delivery conduit has an elongated cross sectional shape, wherein the delivery conduit comprises a plurality of lumens operable to transfer the reduced pressure from the reduced pressure source to the reduced-pressure interface, and wherein at least one wall of each of the plurality of lumens has a protrusion operable to prevent the lumen from collapsing.

10. The system of claim 1, further comprising:
 a securing member operable to secure the insole adjacent the tissue site
11. The system of claim 1, wherein the void is adapted to be adjacent the tissue site, and wherein the reduced pressure is adapted to be applied to the tissue site via the void.

* * * * *